United States Patent
Zedalis et al.

(10) Patent No.: US 8,770,201 B2
(45) Date of Patent: Jul. 8, 2014

(54) CONDOM WITH MULTIFUNCTIONAL COATING

(75) Inventors: Michael S. Zedalis, Mendham, NJ (US); Beng Sim Chuah, Petaling Jaya (MY); David M. Lucas, Petaling Jaya (MY); Angela M. Shiokawa, Sao Roque (BR); Jose R. Siqueira, Sorocaba (BR); Dave Narasimhan, Flemington, NJ (US)

(73) Assignee: GlycoBioSciences Inc., Georgetown (CA)

( * ) Notice: Subject to any disclaimer, the term of this patent is extended or adjusted under 35 U.S.C. 154(b) by 860 days.

(21) Appl. No.: 12/256,648

(22) Filed: Oct. 23, 2008

(65) Prior Publication Data

US 2009/0107513 A1    Apr. 30, 2009

Related U.S. Application Data

(60) Provisional application No. 60/982,928, filed on Oct. 26, 2007.

(51) Int. Cl.
| | | |
|---|---|---|
| *A61F 6/02* | (2006.01) | |
| *A61F 6/04* | (2006.01) | |
| *A61K 31/74* | (2006.01) | |
| *A61K 9/00* | (2006.01) | |
| *A01N 25/08* | (2006.01) | |
| *A61F 6/06* | (2006.01) | |
| *A61K 9/54* | (2006.01) | |
| *A61K 9/56* | (2006.01) | |
| *A41D 19/00* | (2006.01) | |
| *B05D 3/00* | (2006.01) | |
| *A01N 57/26* | (2006.01) | |
| *A61K 31/675* | (2006.01) | |
| *C10M 129/76* | (2006.01) | |
| *B21B 45/02* | (2006.01) | |

(52) U.S. Cl.
USPC ........... 128/844; 128/842; 128/917; 128/918; 424/400; 424/409; 424/430; 424/458; 424/489; 424/78.02; 424/78.03; 427/2.3; 514/81; 514/960; 514/964; 514/965; 602/902; 508/501; 508/583; 508/591

(58) Field of Classification Search
CPC ........... A61F 5/44; A61F 5/441; A61F 5/442; A61F 5/443; A61F 5/451; A61F 5/453; A61F 6/02; A61F 6/04; A61F 6/20; A61K 9/00; A61K 9/002; A61K 9/0012; A61K 9/0014; A61K 9/06; A61K 9/08; A61K 9/10; A61K 9/127; A61K 9/14; A61K 9/143; A61K 9/16; A61K 9/167; A61K 9/1676; A61K 31/00; A61K 31/185; A61K 33/00; A61K 47/00; A61K 47/06; A61K 47/26; B05D 3/00; B05D 3/002; B05D 5/08; B05D 2201/00; B05D 2201/02; B05D 2203/00; B05D 2203/30; B05D 2254/00; B05D 2254/02; B05D 2254/04; B05D 2254/06; B05D 2401/00; B05D 2401/20; B05D 2401/30; B05D 2401/31; B05D 2401/32; B05D 2520/00; B05D 2520/05; B05D 2701/00; B05D 2701/20; C10M 1/00; C10M 1/08; C10M 109/00; C10M 109/02
USPC .................. 128/842–844, 917–918; 602/902; 427/2.3; 206/69; D24/105; 600/38–41; 514/960, 964–965; 424/400, 409, 430, 424/458, 489, 78.02, 78.03
See application file for complete search history.

(56) References Cited

U.S. PATENT DOCUMENTS

| | | | |
|---|---|---|---|
| 4,930,522 | A | 6/1990 | Busnel et al. |
| 4,983,404 | A | 1/1991 | Raman et al. |
| 5,005,695 | A | 4/1991 | Tennefos et al. |
| 5,024,852 | A | 6/1991 | Busnel et al. |
| 5,097,697 | A | 3/1992 | Carnal et al. |
| 5,323,544 | A | 6/1994 | Osgood |
| 5,549,924 | A | 8/1996 | Shlenker et al. |
| 5,885,591 | A | 3/1999 | Ahmad et al. |
| 5,888,441 | A | 3/1999 | Milner |
| 5,922,336 | A | 7/1999 | Tebbe |
| 5,977,223 | A | 11/1999 | Ryan et al. |

| | | | | | | |
|---|---|---|---|---|---|---|
| 5,985,860 | A | 11/1999 | Toppo | 2006/0141165 A1 | 6/2006 | Hassan et al. |
| 6,007,836 | A | 12/1999 | Denzer | 2006/0188528 A1 | 8/2006 | Chuah et al. |
| 6,036,977 | A | 3/2000 | Drizen et al. | 2006/0189493 A1 | 8/2006 | Chuah et al. |
| 6,075,081 | A | 6/2000 | Nile et al. | 2007/0104766 A1 | 5/2007 | Wang et al. |
| 6,139,848 | A | 10/2000 | Ahmad et al. | 2007/0287714 A1 | 12/2007 | Ahmad et al. |
| 6,196,227 | B1 | 3/2001 | Tsushima | 2008/0210580 A1 | 9/2008 | Harrison |
| 6,251,436 | B1 | 6/2001 | Drizen et al. | | | |
| 6,290,981 | B1 | 9/2001 | Keefer et al. | | | |
| 6,306,514 | B1 | 10/2001 | Weikel et al. | | | |

FOREIGN PATENT DOCUMENTS

| | | |
|---|---|---|
| WO | WO-03/09252 A1 | 11/2003 |
| WO | WO-03/092650 A1 | 11/2003 |
| WO | WO-03/092651 A1 | 11/2003 |

OTHER PUBLICATIONS

"PCT International Search Report mailed Dec. 24, 2008 for International Application No. PCT/US2008/081083", 4 pages.

"PCT Written Opinion mailed Dec. 24, 2008 for International Application No. PCT/US2008/081083", 8 pgs.

* cited by examiner

Primary Examiner — Patricia Bianco
Assistant Examiner — Brandon L Jackson
(74) Attorney, Agent, or Firm — Gilbert's LLP; Matthew D. Powell (57) ABSTRACT

Condoms having an elastomeric layer and coating containing an anhydrous warming lubricant and at least one or more ingredients dispersed therein, the coating being disposed on one or both surfaces are provided. The ingredients disposed on the elastomeric layer can be solid particles or encapsulated ingredients that are insoluble in the anhydrous warming lubricant and soluble in water. Methods of producing and using these condoms are also provided.

39 Claims, 5 Drawing Sheets

- 6,347,409 B1 2/2002 Nile et al.
- 6,352,666 B1 3/2002 Nile et al.
- 6,378,137 B1 4/2002 Hassan et al.
- 6,428,791 B1 8/2002 Lezdey et al.
- 6,514,536 B2 2/2003 Drizen et al.
- 6,541,030 B2 4/2003 Vaghefi
- 6,620,942 B2 9/2003 Yeh et al.
- 6,624,198 B1 9/2003 Porat
- 6,664,296 B1 12/2003 Meignant
- 6,709,725 B1 3/2004 Lai et al.
- 6,840,244 B2 1/2005 Kemp
- 6,939,569 B1 * 9/2005 Green et al. .......... 424/667
- 7,005,408 B2 2/2006 Ahmad et al.
- 7,037,579 B2 5/2006 Hassan et al.
- 7,064,114 B2 6/2006 Yiv et al.
- 7,084,884 B1 8/2006 Nelson
- 7,157,393 B2 1/2007 Gromelski et al.
- 7,176,238 B1 2/2007 Garvey et al.
- 7,214,390 B2 5/2007 Barone, Jr. et al.
- 7,235,505 B2 6/2007 Gromelski et al.
- 7,285,517 B2 10/2007 Ahmad et al.
- 7,405,186 B2 7/2008 Harrison
- 7,417,013 B2 8/2008 Ahmad et al.
- 2003/0161975 A1 8/2003 Lucas et al.
- 2003/0211161 A1 11/2003 Ahmad et al.
- 2004/0115250 A1 6/2004 Loo et al.
- 2004/0167039 A1 8/2004 Ahmad et al.
- 2004/0185065 A1 9/2004 Ahmad et al.
- 2005/0042248 A1 2/2005 Ahmad et al.
- 2005/0042249 A1 2/2005 Ahmad et al.
- 2005/0066414 A1 3/2005 Yu et al.
- 2006/0070167 A1 4/2006 Eng et al.
- 2006/0094608 A1 5/2006 Ahmad et al.

Fig. 1

Fig. 2
Inverted Image of Fig. 1

Fig. 3

Fig. 4
Inverted Image of Fig. 3

CONDOM WITH MULTIFUNCTIONAL COATING

CROSS REFERENCE TO RELATED APPLICATION

This application claims priority under 35 U.S.C. §119(e) to U.S. patent application Ser. No. 60/982,928, filed Oct. 26, 2007, which is hereby incorporated by reference in its entirety

TECHNICAL FIELD

The present invention generally relates to condoms having an anhydrous warming lubricant and at least one or more ingredients disposed on one or more surfaces of the condoms, the lubricant reacting with skin-generated moisture at the same time of contact creating a temperature rise and enhanced effectiveness of one or more ingredients present. Specifically provided are condoms with at least one solid particle or encapsulated ingredient dispersed in the lubricant that is disposed on one or more surfaces of the condom, and methods of use and manufacturing thereof.

BACKGROUND

Condoms and other prophylactics and protective devices provide physical barriers against the transmission of bodily fluids or other fluids. A chemical barrier can also be used alone or in conjunction with a condom to prevent such transmission. In some instances, the chemical barriers serve as a supplemental form of protection in the event the physical barrier is breached.

Chemical barriers, such as lubricants, have been employed for a number of applications, including lubrication of elastomeric condoms and lubrication of skin. More recently, lubricants have been designed to take advantage of the heat that is generated when glycerin and/or propylene glycol are dissolved in water. Unfortunately, glycerin and propylene glycol on their own do not spread readily on skin and other surfaces and can irritate skin after prolonged use, since glycerin extracts water from the skin surface. The spreadability of such lubricants is further compromised by the addition of one or more insulating agents, such as honey, isopropyl myristate and/or isopropyl palmitate, which reportedly help to retain the heat of the lubricant see, e.g., Int'l App. Pub. Nos. WO 03/092652, WO 03/092651, and WO 03/092650 (corresponding to U.S. Pat. Nos. 7,005,408, 7,285,517, 7,417,013 (Ahmad); U.S. Pat. App. Pub. Nos. 2003/0211161, 2004/0167039, 2004/0185065, 2005/0042248, 2005/0042249, US2006/0094608, and 2007/0287714 (Ahmad)) discussed below.

Glycerin and propylene-based alcohols have been used in water soluble condom lubricants. For example, U.S. Pat. No. 6,196,227 to Tsushima discloses water soluble lubricant for a condom and a condom spread with said water soluble lubricant. This lubricant is not indicated to have a warming effect upon contact with skin-generated moisture because the lubricant itself contains water. U.S. Pat. Nos. 5,885,591 and 6,139,848 to Ahmad et al. discloses highly lubricious personal lubricant compositions containing one or more polyhydric alcohols, one or more water-soluble polymers derived from cellulose, water, and, optionally, preservatives and alkali metal or alkaline earth metal bases. Since these compositions already contain water, no heating or warming reaction occurs when the lubricant is applied to the body and the glycerin comes in contact with body-generated moisture.

U.S. Pat. No. 5,512,289 to Tseng et al. discloses a spermicidal anti-viral lubricant composition containing a water-soluble polymeric gel matrix comprising a hydroxyalkyl cellulose with an alkylphenoxypolyethoxyethanol spermicide and a solubilizing moiety comprising polyethoxylated castor oil. The use of the alkylphenoxypolyethoxyethanol spermicide prevents collapse of the hydroxyalkyl cellulose gel. The spermicidal composition can be dispersed by use of a pharmaceutically acceptable vehicle, such as water, alcohols, e.g., ethanol, glycerin, propylene glycol, and mixtures thereof. A typical formulation of the spermicidal lubricant can include water 75.50 wt %, glycerin 17.00 wt %, hydroxyethyl cellulose 1.00 wt %, polyvinyl pyrrolidone 0.90 wt %, carboxymethyl cellulose 1.00 wt %, Nonoxynol-9 spermicide 2.00 wt %, polyethoxylated castor oil 2.00 wt %, methylparaben 0.20 wt %, sorbic acid 0.05 wt %, and citric acid 0.35 wt %. Since glycerin and glycol are already dissolved in water, the lubricant does not provide a warming effect.

Warming lubricants that contain glycerin and other polyhydric alcohols are known in the prior art. For example, Int'l App. Pub. Nos. WO 03/092651 and WO 03/092652 to Ahmad et al. (see also U.S. Pat. Nos. 7,005,408 and 7,417,013; U.S. Pat. App. Pub. Nos. 2003/0211161 and 2006/0094608) disclose warming and nonirritating lubricating compositions containing polyhydric alcohols and an insulating agent. The polyhydric alcohol comprises glycerin, alkylene glycol, or a mixture thereof. The alkylene glycol is selected from the group consisting of propylene glycol, butylene glycol and hexalene glycol, whereas the polyethylene glycol is selected from the group consisting of polyethylene glycol 300 and polyethylene glycol 400. The insulating agent is selected from the group consisting of honey, isopropyl myristate and isopropyl palmitate. A warming action is created by the heat released during dissolution of the polyhydric alcohol in water, and the insulating agent retains the heat. All compound selected for addition to the anhydrous warming lubricant are both water and glycol soluble and therefore no particles are present in the warming lubricant.

Spreadable warming lubricants are provided in U.S. Pat. App. Pub. Nos. 2006/0188528 (Chuah) and 2006/0189493 (Chuah). These lubricants are substantially anhydrous, comprising a mixture of glycerin, polyhydric alcohol, and a nonionic surfactant, and, for a thickened lubricant, a carbomer thickener can be used.

U.S. Pat. App. Pub. No. 2005/0076916 to Barder discloses a condom. The condom has a vasodilator active compound applied to its external surface, preferably disposed towards the open end of the condom to alleviate symptoms associated with female sexual dysfunction. The lubricant used is water-based with a pH in the range of 3 and 5. Thus, the lubricant used is not a warming lubricant.

U.S. Pat. No. 6,840,244 to Kemp discloses condom with an erectogenic composition. The condom has an erectogenic vasodialtor compound immobilised at the head end on the interior condom surface. The erectogenic compound can be dispersed or dissolved in a gel carrier comprising a thickened liquid medium. The condom may also include a lubricant, which is immiscible with the erectogenic compound or composition. The erectogenic compound is not provided as an insoluble particle dispersed in a warming lubricant, but rather it is localized at the head end of the condom. When the lubricant is water based, the thickened liquid medium preferably comprises a vegetable oil, for example castor oil, to achieve immiscibility. When the lubricant is oil based, the medium preferably comprises a polyhydroxy compound such as propylene glycol. The vasodilator is selected from nitrates, long and short acting alpha-adrenoceptor blockers, ergot alkaloids, anti-hypertenives and the prostaglandins. The lubricant is not a warming lubricant.

U.S. Pat. No. 7,405,186 to Harrison discloses lubricant compositions, condom products and methods of making same. The warming lubricant includes about 50% by weight of an anhydrous polyalkylene glycol component, comprising two different molecular weights of polyalkylene glycol, remaining comprising a viscosity inducing cellulosic derivative. It is indicated that the lubricant may comprise vasodilators such as methyl nicotinate or histamine hydrochloride. Both methyl nicotinate and histamine hydrochloride are soluble in both water and alcohols and will not result in an active vasodilator particle dispersed in the warming lubricant due to their solubility therein.

U.S. Pat. No. 6,290,981 to Keefer, et al. discloses the use of nitric oxide-releasing agents to treat impotency. This method involves the administration of nitric oxide by a nitric oxide-releasing agent that can be a polyether comprising at least one nitric oxide-releasing functional group. Also provided are nitric oxide delivery means, such as transurethral applicator, penile implant, dermal patch or condom, for use in the method.

U.S. Pat. No. 7,214,390 to Barone, Jr., et al. discloses topical compositions for enhancing sexual responsiveness. This topical composition enhances sexual responsiveness of a mammal and comprises an effective dosage of a peripheral vasodilator, an absorption enhancer, a vasoconstrictor, an alpha receptor blocker are combined with a pharmaceutically-acceptable topical vehicle to produce the composition. The composition can comprise a) about 1% methyl nicotinate, b) about 25 drops of an alcohol extract of yohimbe, c) about 8 mg/cm$^3$ of L-arginine, d) about 12 drops of an alcohol extract of muira puama, e) about 12 drops of an alcohol extract of catuaba, f) about 12 drops of an alcohol extract of maca, and g) about 12 drops of an alcohol extract of saw palmetto, wherein a) through g) are in a pharmaceutically-acceptable water-based topical vehicle comprising aloe and vitamin E. This water-based composition has no warming effect.

There is a therefore need for an improved condom with a lubricant having greater functionalities and enhanced effects than currently available lubricated condoms.

SUMMARY

Condoms having a warming lubricant and an active ingredient are provided wherein there is at least one ingredient dispersed in the warming lubricant and this ingredient is provided in a highly effective and concentrated form contacting a user's skin by dissolution or release of active ingredient by skin-generated moisture. This local concentration of the active ingredient on the skin provides greater effectiveness as compared to if the active ingredient had been dissolved completely in the original lubricant. Reference to a highly effective and concentrated form means that upon initial contact, a warming action occurs and a local concentration of the dissolved active ingredient approaches the limits of saturation in the available moisture on the skin. Due to the ability to locally concentrate the active ingredient, less active ingredient is needed in the lubricant than would be needed if the active ingredient had been dissolved in the original lubricant and the active ingredient is thus highly effective since is it not diluted.

Other embodiments of the present invention include a condom having a coating of an anhydrous warming lubricant in combination with at least one or more active ingredients that is either solid or encapsulated in a water soluble capsule shell and the active ingredient is insoluble in the warming lubricant and is readily soluble in water. Suitable warming lubricants contain, for example, glycerin in an amount from about 40% to 60%, a polyhydric alcohol in an amount from about 40% to 60%, and a non-ionic surfactant in an amount from about 0.1% to 10%. One suitable spreadable warming lubricant is provided in U.S. Pat. App. Pub. No. 2006/0188528 (Chuah), the disclosure of which is hereby incorporated by reference in its entirety. A suitable thickened spreadable warming lubricant is provided in U.S. Pat. App. Pub. No. 2006/0189493 (Chuah), the disclosure of which is hereby incorporated by reference in its entirety.

When skin-generated moisture contacts the coating, a moisture gradient is established between the skin and the warming lubricant where the moisture content decreases progressively as a function of distance from the skin. The skin-generated moisture reacts with the warming lubricant, releasing the heat of dissolution of the anhydrous warming lubricant and, thereby, increasing the lubricant temperature (~4° C.) in the region adjacent to the skin. The solid particles or encapsulates of active ingredients adjacent to the skin are then quickly and substantially simultaneously dissolved or released into the skin-generated moisture adjacent to the skin. The combination of temperature rise, which aids to expand the skin pores, and the localized high concentration of active ingredient, enables quick absorption of the active ingredient into the skin, thereby creating simultaneous and synergistic enhanced effect of the active ingredient as compared to the absence of the warming lubricant. Moreover, the dissolution of the active ingredient by a small amount of skin-generated moisture generally results in highly concentrated solution of the active ingredient resulting in rapid more effective synergistic action of the active ingredient. Due to its lubricant-insolubility and the water-solubility, the active ingredient is made available in localized high concentrations upon contact with skin-generated moisture by dissolution therein. As a result, only a small concentration of the active ingredient in the overall anhydrous warming lubricant composition is needed for providing effective performance, which is unlike lubricant compositions that use completely dissolved active ingredients.

Some embodiments of such condoms are made of an elastomeric layer such as natural rubber latex, synthetic polyisoprene, guayule, polyurethane, or combinations and copolymers thereof. Examples of the active insoluble ingredients added to the anhydrous warming lubricant include an antibiotic compound, a microbicide, a sexual enhancement lubricant, a warming lubricant, a vasodilator, a spermicide, a skin conditioner, a flavoring, and/or a fragrance each of which are provided either as an insoluble solid particle or as an encapsulated ingredient. One or more specific embodiment includes a condom having an anhydrous warming lubricant in combination with solid particles of L-arginine disposed on both the inner and outer surfaces of the elastomeric condom. Other embodiments have the at least two ingredients, one of which is an anhydrous warming lubricant disposed only on the inner surface or only on the outer surface of the elastomeric layer of the condom. In one or more embodiments of the present invention, at least one ingredient is encapsulated and the active ingredient is released by skin generated moisture dissolution of encapsulated capsule wall. A suitable encapsulation wall member is gelatin, and/or hydroxyalkyl cellulose all of which exhibit good water solubility and insolubility in polyhydric glycols.

In accordance with one aspect of the present invention, the elastomeric layer of some condoms has a warming lubricant comprising glycerin and polypropylene glycol with minimal water content and discrete particles of L-arginine vasodilator that remains stable in the anhydrous lubricant without dissolution. When the condom with anhydrous warming lubricant and solid particles of L-arginine contacts small quantity of skin generated moisture, warming of the lubricant occurs due to release of heat solution of glycerin and polypropylene glycol. The L-arginine solid particles dissolve at the same time producing a highly concentrated solution of L-arginine producing enhanced release of nitrous oxide within the tissue. The warming effect enlarges skin pores permitting easy penetration of concentrated solution of L-arginine into skin and tissue. Due to this generation of an L-arginine-concentrated solution, the amount of L-arginine in the overall lubricant composition can be smaller as compared to a composition where the L-arginine is dissolved in its entirety into the lubricant solution.

Addition of other ingredients that are water-soluble and are insoluble in anhydrous warming lubricant such as a microbicide, a sexual enhancement lubricant, a spermicide, a skin conditioner, a flavoring and a fragrance will have similar functionality. Examples of such compounds include most antibiotics such as tetracycline, microbicides such as chlorohexidine gluconate etc., sweeteners and flavoring agents that belong to this class include sucrose, dextrose dextrins, maltose, trehalose, D-tagatose, dried inver sugar, ribose, fructose, levulose, galactose, glucose, maltodextrin, polydextrose, isomalt, sorbitol, sorbitol syrup, mannitol, xylitol, hexa-resorcinol, maltitol, isomaltol erythriol, lactitol, xylose, tagatose and hydrogenated starch hydrolysates (maltitol syrup). The high potent sweeteners includes the dipeptides aspartame,neotame and alitame; N-sulfonylamides such as saccharin including the salts thereof and acesulfam including the salts thereof, sulfamates such as cyclamate including the salts thereof, chlorinated sugar derivatives such as ) sucralose; Terpenoid glycosides such as Rebaudioside-A Stevioside and Glyhyrrhizin; proteins such as thaumatin and monellin and Di-hydrochalcones. A variety of one or more flavoring agents may be used. Flavoring agents suitable include natural, natural-identical, and/or artificial flavoring substance, or mixtures thereof. Some examples of suitable tastes are peppermint, lemon, and orange.

When the active ingredient is encapsulated in a capsule the wall that dissolves readily in the presence of skin-generated moisture (and is insoluble in the anhydrous warming lubricant), the capsule may be used to contain liquid active ingredients and/or solid active ingredients that are soluble in the anhydrous warming lubricant. Typically, the wall of a microcapsule may be a gelatin gel, and/or hydroxyalkyl cellulose, or combinations thereof.

In accordance with one aspect of the present invention, the elastomeric layer of some condoms has a thickness of no more than about 0.05 mm. Other aspects of the present invention include condoms with elastomeric layers that are contoured to have a larger diameter at defined portions of the condom, or otherwise have a textured surface.

In accordance with at least one aspect of the present invention, a method for manufacturing a condom having an anhydrous warming lubricant and at least one ingredient disposed on the elastomeric layer is also provided. An embodiment of such methods includes the steps of forming an elastomeric layer from either natural rubber latex, synthetic polyisoprene, guayule, polyurethane, or combinations thereof, into the shape of a condom; and disposing an anhydrous warming lubricant and at least one ingredient on the elastomeric condom wherein the second ingredient may include a microbicide, a sexual enhancement lubricant, a vasodilator, a spermicide, a skin conditioner, a flavoring, and a fragrance. One embodiment of the present invention further includes the step of disposing at least one of the ingredients on both the inner and outer surfaces of the elastomeric layer in combination with an anhydrous warming lubricant, while other embodiments include the step of disposing more than one ingredient on the inner or outer surface only.

Still other embodiments include an additional step of encapsulating at least one of the ingredients prior to disposition on the elastomeric layer, wherein the encapsulated ingredient disposed on the elastomeric layer is exposed (i.e., uncovered by any other layer of latex). One or more embodiments also include a step of forming a film on the elastomeric layer prior to application of the encapsulated ingredient, followed by application of the encapsulated ingredient to the layer of film. These embodiments also allow for the encapsulated ingredient to remain exposed after application.

Other embodiments of the present invention include a method for producing a condom having an anhydrous warming lubricant and particles of L-arginine disposed therein that remains stable in the condom package indefinitely. The particles of L-arginine are added to anhydrous warming lubricant and distributed by standard mixing method. In an alternate manufacturing method, the L-arginine is dissolved in a small quantity of water and adding this small volume of L-arginine concentrated solution to anhydrous warming lubricant results in the extraction of water from the concentrated L-arginine solution permitting immediate precipitation of fine particles of L-arginine in the almost anhydrous warming lubricant, which has adequate quantity of glycerin and poly propylene glycol. When the anhydrous warming lubricant comprising L-arginine particles contact skin-generated moisture during use, the warming action of the anhydrous warming lubricant and the dissolution of L-arginine particles in the moisture forming concentrated solution of L-arginine in close proximity with the skin and the warming action enlarges skin pores allowing entry of L-arginine into skin tissue. Menthyl lactate may be added to the condom lubricant to provide pleasant sensation.

BRIEF DESCRIPTION OF THE DRAWINGS

FIGS. 2 and 4 are inverted images of FIGS. 1 and 3, respectively;

Before describing several exemplary embodiments of the invention, it is to be understood that the invention is not limited to the details of construction or process steps set forth in the following description. The invention is capable of other embodiments and of being practiced or being carried out in various ways.

DETAILED DESCRIPTION

One or more embodiments of the present invention include a condom having an elastomeric layer with an anhydrous warming lubricant and at least one or more ingredients as insoluble solid particles or insoluble encapsulated capsules disposed on a surface thereof. In some embodiments, the ingredients may include two or more ingredients in combination with an anhydrous warming lubricant. The ingredients can be selected from, but not limited to a microbicide, a sexual enhancement lubricant, a warming lubricant, a vasodilator, a spermicide, a skin conditioner, a flavoring, and a fragrance. A particular ingredient may be used in a particular embodiment for one function and in another for another function.

The term "natural rubber latex" as used in this disclosure encompasses cured elastomeric material sourced from Hevea brasiliensis (the traditional rubber tree), Parthenium argentatum (guayule), sunflower, goldenrod and the like, as well as genetically modified variations of these or other biological sources.

The term "microbicide," as used herein, refers to a substance active against microorganisms or microbes such as bacteria, viruses, yeasts and fungi, including those responsible for sexually transmitted diseases. Microbicide as used herein also refers to substances and includes antimicrobial agents having either or both bactericidal and bacteriostatic properties having the purpose of reducing the infectivity of microorganisms. Such substances should be compatible with mucous membranes and skin. Additionally, the ingredients should not react adversely with any of the other ingredients. When these ingredients are insoluble in anhydrous warming lubricant, they may used as solid particles and when they are soluble therein or provided in a liquid form, these active ingredients will be encapsulated in some embodiments of the present invention. Examples of microbicides used in some embodiments of the present invention include, without limitation, sodium dodecyl sulfate, quaternary ammonium salts, halogenated hydroxy aromatics, chlorhexidine gluconate, triclosan, miconazole, chlortrimazole, as well as pharmacologically acceptable salts thereof. One or more embodiments of the present invention utilize other microbicides known in the art.

The term "warming lubricant," as used herein, refers to a substance which generates or creates the feeling of heat to the skin. In some embodiments, the warming lubricant as disclosed in U.S. Pat. App. Pub. Nos. 2006/0188528 (Chuah) and 2006/0189493 (Chuah) can be utilized and are incorporated by reference in their entirety. In these embodiments, the warming lubricant is substantially anhydrous, and includes substances such as glycerin, polyhydric alcohol and non-ionic surfactants, generating heat upon contact with moisture present on skin surfaces of the user.

The term "vasodilator," as used herein, refers to a substance which, when topically applied, causes vasodilation in the human body, i.e., enhances blood circulation to body parts, increases nitrous oxide levels, generates heat or creates the feeling of heat and/or increases sexual arousal, response or otherwise treats sexual dysfunction. Such substances should be compatible with mucous membranes and skin and should not react adversely with any of the other ingredients, encapsulants and/or films used in some embodiments of the present invention. Embodiments of the present invention utilize vasodilators such as niacin (i.e., nicotinic acid and physiologically compatible derivatives thereof), L-arginine, ginger, menthol, nitric oxide precursors and variations thereof, while other embodiments may utilize other vasodilators known in the art.

The term "spermicide," as used herein, refers to a substance having an effect, which may include, but is not limited to, reduced motility, reduction of numbers, and the like, on human sperm. Compounds such as nonoxynol-9, benzalkonium chloride and lactic acid are recognized in the literature as having spermicidal and reduced sperm motility effects. Such substances should be compatible with mucous membranes and skin and should not react adversely with any of the other ingredients, encapsulants used in some embodiments of the present invention.

The term "skin conditioner," as used herein, refers to a substance having moisturizing, anti-inflammatory, or other therapeutic qualities. Further, the term "skin conditioner" includes substances including, but not limited to, aloe vera, polybutylene, fatty acids and derivatives thereof, dimethicone, glycerin, polyhydric glycols and the like, which help prevent or treat skin conditions such as dry skin, loss of skin elasticity and collagen content. Such substances should be compatible with mucous membranes and skin and should not react adversely with any of the other ingredients, encapsulants used in some embodiments of the present invention. Various embodiments of the present invention utilize skin conditioners such as aloe vera, glycerin, and propylene glycol while other embodiments may incorporate other skin conditioners known in the art.

The term "sexual enhancement lubricant", as used herein, refers to a substance which creates a desensitizing or numbing effect to the localized area of application to the skin. Examples of such materials include, but are not limited to, "caine" anesthetics such as tetracaine, lidocaine and benzocaine; promoxine; menthol; and compatible combinations thereof. Such substances should be compatible with mucous membranes and skin and should not react adversely with any of the other ingredients and/or encapsulants used in some embodiments of the present invention.

Any ingredients used on the surface of a condom on the present invention should be compatible with mucous membranes and skin should not react adversely with any of the other ingredients, encapsulants used in some embodiments of the present invention. The ingredients used in any embodiment of the present invention should not have adverse effects on the users and should be safe for all uses. Further, the ingredients used in any embodiment can be in any form, including without limitation, substantially anhydrous, aqueous, emulsified, encapsulated, adsorbed, absorbed, solubilized, finely divided, as well as compatible combinations thereof.

Further embodiments of the invention include one or more ingredients that are encapsulated. In some embodiments, such encapsulated ingredients have encapsulant walls that are insoluble in anhydrous warming lubricant but dissolve readily in skin-generated moisture, thereby rapidly releasing the contents of the encapsulated capsule. This encapsulation procedure enables use of liquid active ingredients and active ingredients that readily dissolve in an anhydrous warming lubricant. The cell walls having this property can be made from gelatin, and/or hydroxyalkyl cellulose. In accordance with the present invention, the capsules can be of any size, including in the range of about 1 to 1000 micrometers and in the range of about 1 to 1000 nanometers in length.

U.S. Pat. No. 6,541,030 (Vaghefi), and the references cited therein, disclose methods of encapsulation as well as compounds suitable for encapsulation of various ingredients suitable for use on one or more surfaces of the condom of the present invention. U.S. Pat. No. 4,983,404 (Raman) also discloses the use of encapsulation to control the release of compounds suitable for use on one or more of the surfaces of the condom of the present invention. These patents and the references cited therein are incorporated by reference in their entireties into the present disclosure.

Embodiments of the present invention include condoms having an elastomeric layer wherein at least one or more ingredients in combination with an anhydrous warming lubricant are disposed in any combination and on any layer. One or more examples of the present invention have at least one ingredient disposed on both the inner and outer surface of the elastomeric layer, while other examples have the at least two ingredients disposed on only the inner surface or the outer surface of the elastomeric layer. In yet other embodiments, at least one of the two ingredients disposed on the elastomeric layer is encapsulated. Further, some embodiments also include an encapsulated ingredient disposed on one or both layers.

Figure 1:
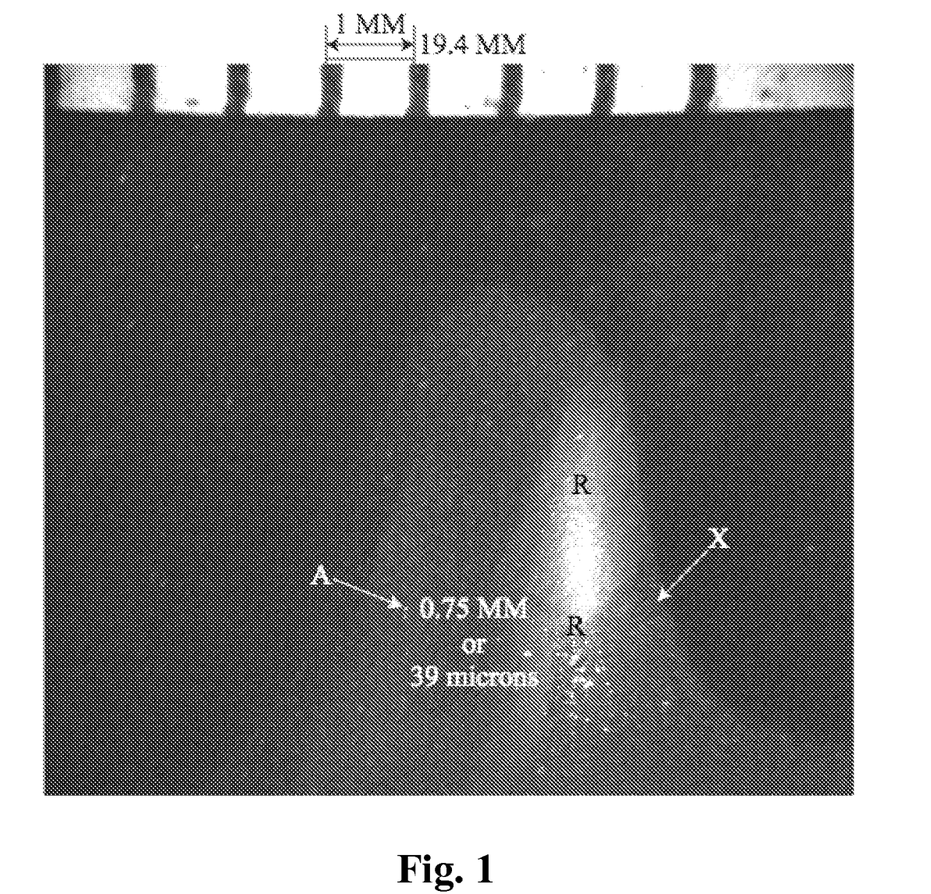
FIGS. 1, 2, 3, and 4 are micrographs of one embodiment of the present invention, where an active ingredient is solid particles of L-arginine that is not soluble in a warming lubricant is shown on a condom external surface.
Figure 2:
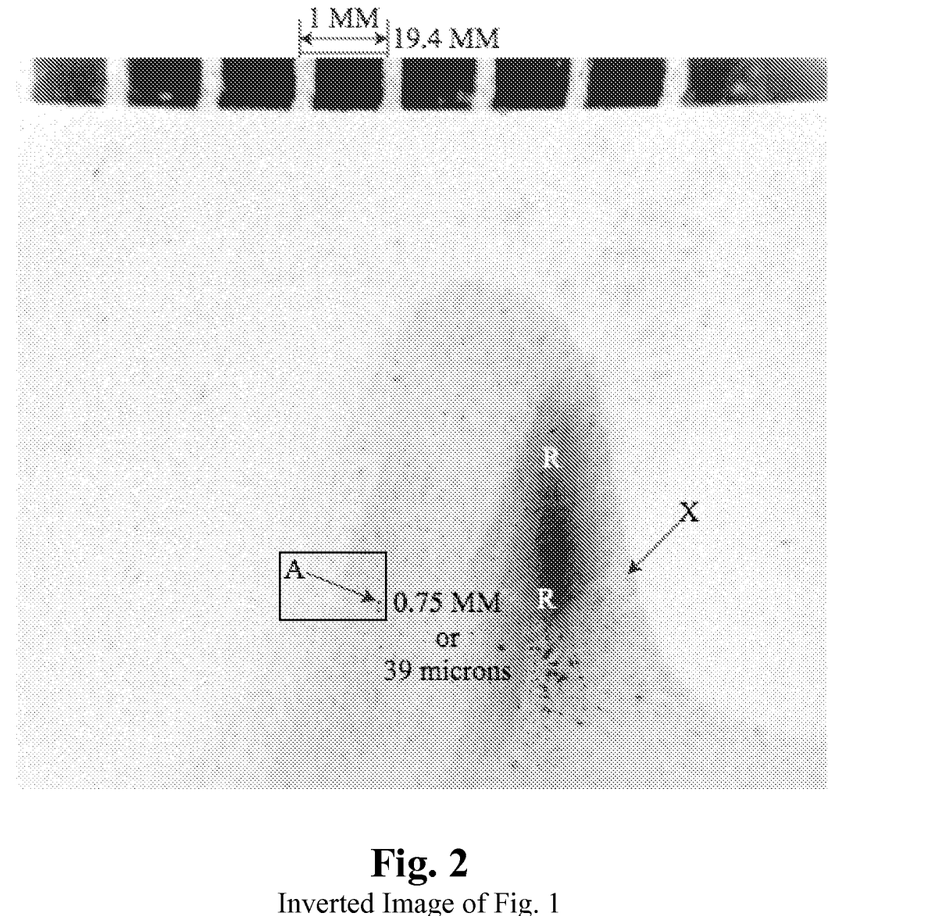
Figure 3:
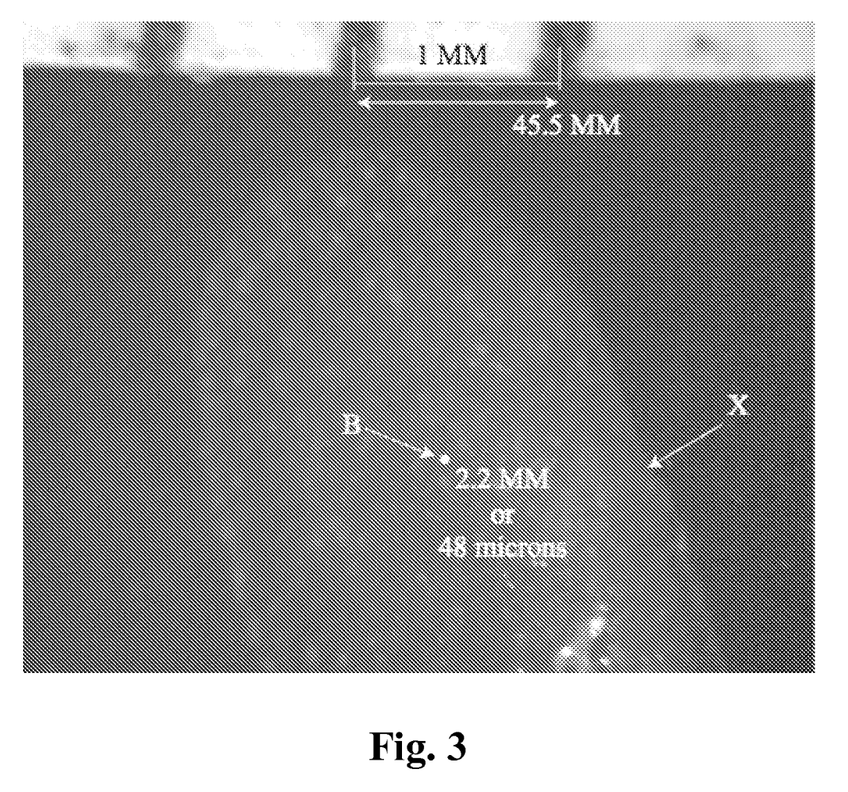
Figure 4:
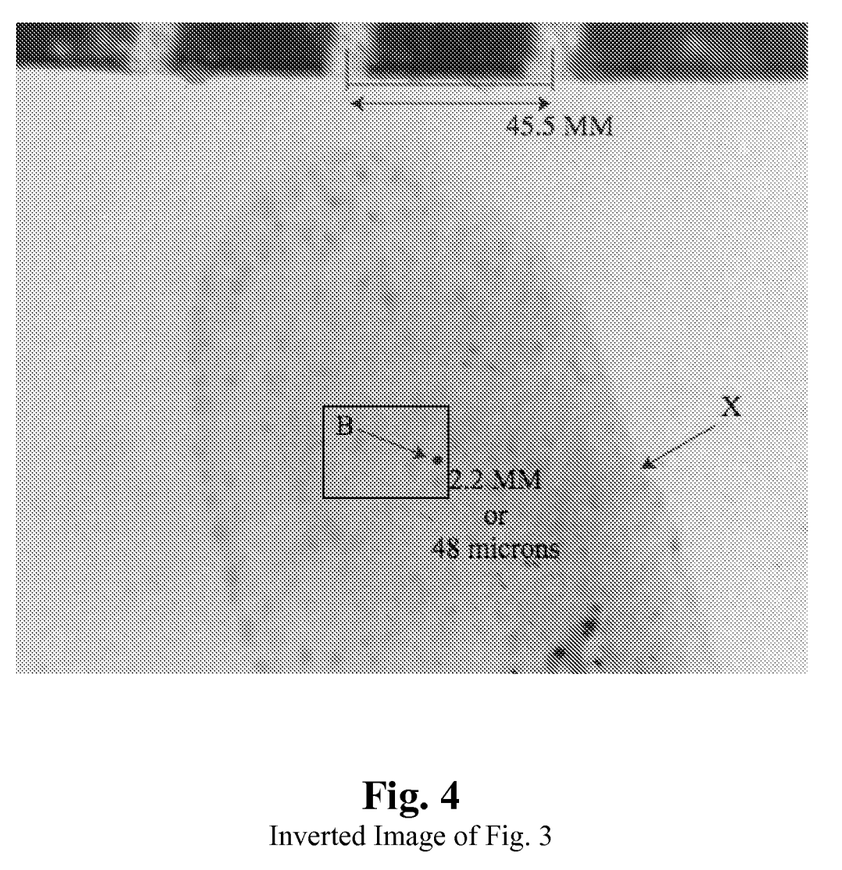

In FIGS. 1, 2, 3, and 4, micrographs that show an active ingredient, L-arginine, that is not soluble in a warming lubricant on a condom surface are provided. Example 29 details the method of producing this condom having an anhydrous warming lubricant with solid insoluble particles of L-arginine. FIGS. 1 and 3 provide micrographs of a condom surface having a warming lubricant that shows particles of L-arginine being suspended therein. In FIGS. 1 and 2, a 1 mm scale represents 19.4 mm on the actual condom. In FIGS. 3 and 4, a 1 mm scale represents 45.5 mm. A reference circle of a known size, item "A" in FIGS. 1 and 2, and item "B" in FIGS. 3 and 4, is shown which was then compared readily with the size of particles of L-arginine present. In FIGS. 1 and 2, the particle size is approximately 39 microns, and in FIGS. 3 and 4, the particle size is approximately 48 microns. FIGS. 2 and 4 are inverted images of FIGS. 1 and 3, respectively, to aid in discerning the details of the micrographs. The white solid insoluble particles of FIGS. 1 and 3 appear black in FIGS. 2 and 4. The black non-reflecting condom surface of FIGS. 1 and 3 appears white in FIGS. 2 and 4 for improved appearance. In producing these micrographs, the condom was cut as a flat strip and placed on a dark flat surface and was viewed and photographed using Olympus SZ-III stereomicroscope. The illuminating light was placed at an acute angle to the surface to highlight the undissolved solid particles of L-arginine present. An air bubble in the condom is shown at X and the bright reflection of the light is seen along RR. The particles of insoluble L-arginine are clearly seen in the region of the bubble where the illuminating light is at a sharp acute angle.

Figure 5:
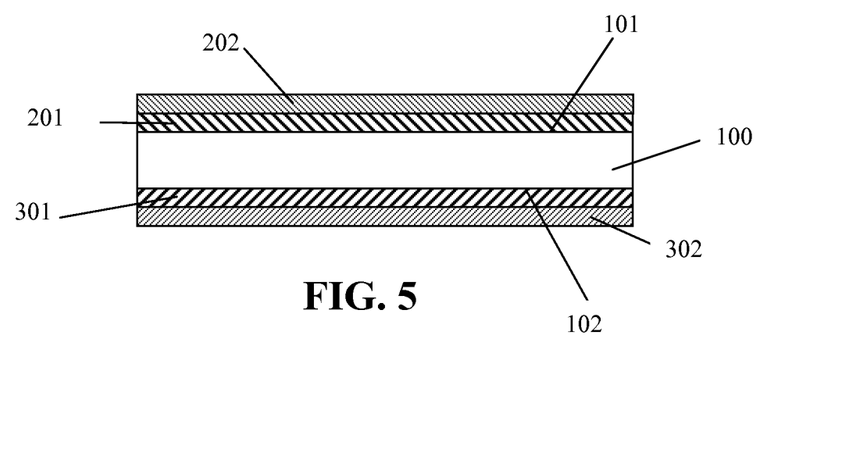
FIG. 5 is a partial cross-sectional view of an embodiment of a condom having an elastomeric layer with anhydrous warming lubricant and one active ingredient disposed on both its inner and outer surfaces.

Turning to other examples, in FIG. 5, the elastomeric layer 100 having an inner surface 101 and outer surface 102. A microbicide 201 and an anhydrous warming lubricant 202 are disposed on the inner surface 101 of the elastomeric layer 100 and a microbicide 301 and an anhydrous warming lubricant are 302 disposed on the outer surface 102.

Without intending to be bound by theory, it is believed that the presence of substances which generate or produce heat increase effectiveness of the active ingredients. For example, a warming lubricant generates heat upon contact with moisture present on the skin or membranes of the user enhancing the activity of vasodilators, for example, by opening skin pores to permit the vasodilator to enter the skin. It is thought that this generated heat may enhance the release of a fragrance used as an active ingredient by increasing its volatility. The volatilized fragrance then diffuses into the immediate environment.

Figure 6:
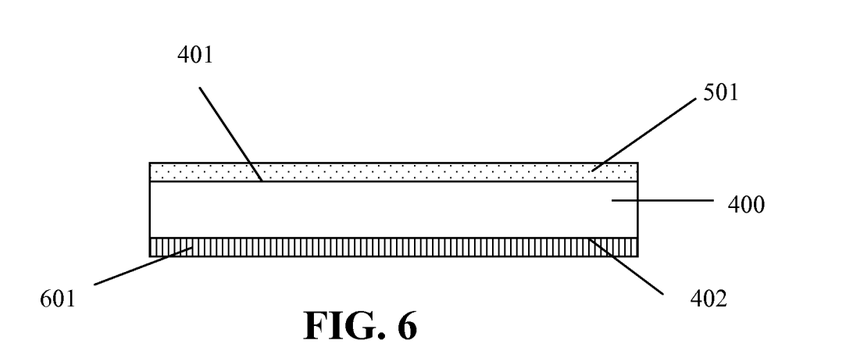
FIG. 6 is a partial cross-sectional view of an embodiment of a condom having an elastomeric layer with one ingredient disposed in an anhydrous warming lubricant on its inner surface and one ingredient in an anhydrous warming lubricant disposed on its outer surface, wherein one of the ingredients disposed on the inner surface is encapsulated.

In accordance with FIG. 6, the elastomeric layer 400 has an inner surface 401 and an outer surface 402. The inner surface 401 of FIG. 2 carries an encapsulated sexual enhancement lubricant 501 in an anhydrous warming lubricant. Further, outer surface 402 carries spermicide in an anhydrous warming lubricant without encapsulation 601. Other ingredients can be substituted for ingredients 501 and 601. Further, additional ingredients can be added. These ingredients can be provided in a carrier base.

Figure 7:
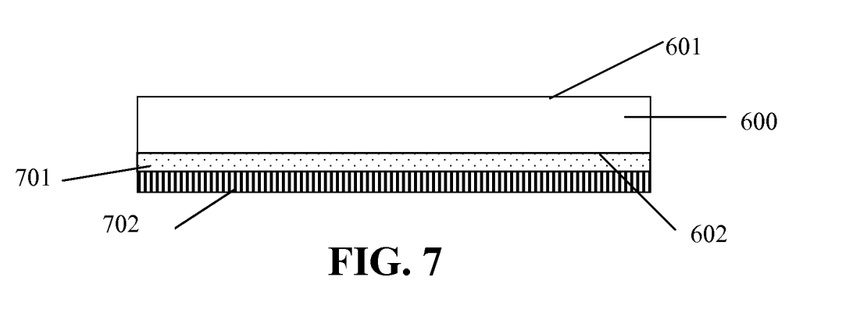
FIG. 7 is a partial cross-sectional view of an embodiment of a condom having an elastomeric layer with two ingredients in an anhydrous warming lubricant disposed on its outer surface only, wherein one of the ingredients is encapsulated.

In accordance with FIG. 7, the elastomeric layer 600 has an inner surface 601 and an outer surface 602, wherein the inner surface carries no ingredient. The outer surface 602 of FIG. 4, however, has an encapsulated vasodilator 701 and an unencapsulated spermicide 702 in an anhydrous warming lubricant.

Embodiments of the present invention also include the following combination of ingredients on the inner and outer surface, only the inner surface and/or only the outer surface of the elastomeric layer. In particular embodiments, when materials are present on both the inner and outer surfaces of the condom, the materials on one or the other surface may be the same or different. In the examples, a condom formed from a cured natural rubber latex is used as an example. A condom formed from other elastomeric materials such as polyvinylchloride, polychloroprene, polyurethane, copolymers of elastomeric materials and the like may also be used and is considered within the scope of the invention.

The lubricious material referred to in the examples below in the anhydrous warming lubricant that serves as a carrier for one or more active ingredients and may be a modified cellulosic material, such as a carboxy or hydroxy cellulose, cellulosic derivatives, and the like; a "dry" silicone based material such as polydimethyl siloxanes; an anhydrous material that functions by contact with moisture present on the skin or membranes of the users; and combinations of these materials with other materials known to those skilled in the art of personal lubricants.

EXAMPLES

A series of examples of condoms of the invention having an anhydrous warming lubricant and at least one or more ingredients present is shown below. These and other exemplary ingredients may be present in larger or smaller quantities on one or more surfaces of the condom for particular applications and are as follows:

Example 1

A microbicide and a sexual lubricant are combined with a carrier and applied to one or more surfaces of a condom. A condom may have between about 0.5 to about 1.0 ml of a lubricious material on a surface(s) which includes between about 0.1 to about 5% (w/w) chlorhexidene gluconate, a microbicide, and between about 0.1 to about 10% (w/w) of a menthol-based sexual enhancement lubricant.

Example 2

A microbicide and a warming agent are combined with a carrier and applied to one or more surfaces of a condom. A condom may have between about 0.5 to about 1.0 ml of a lubricious material on a surface(s) which includes between about 2 to about 5% (w/w) of chlorhexidene gluconate, a microbicide, and between about 0.1 to about 75% of a substantially anhydrous mixture of glycerin, propylene glycol and a surfactant, a mixture reported to exhibit warming upon contact with moisture.

Example 3

A microbicide and a vasodilator are combined with a carrier and applied to one or more surfaces of a condom. The condom may have between about 0.5 to about 1.0 ml of a lubricious material on a surface(s) which includes between about 2 to about 5% (w/w) of benzalkonium chloride, a microbicide, and between about 0.1 and about 10% (w/w) of niacin, a vasodilator.

Example 4

A microbicide and a spermicidal agent are combined with a carrier and applied to one or more surfaces of a condom. The condom may have between about 0.5 to about 1.0 ml of a lubricious material on a surface(s) which includes between about 2 to about 5% (w/w) of chlorhexidene gluconate, a microbicide, and between about 0.1 to about 10% (w/w) of nonoxynol-9, a spermicidal agent.

Example 5

A microbicide and a skin conditioner are combined with a carrier and applied to one or more surfaces of a condom. The condom may have between about 0.5 to about 1.0 ml of a lubricious material on a surface(s) which includes between about 2 to about 5% (w/w) of chlorhexidene gluconate, a microbicide, and between about 0.1 to about 10% (w/w) of glycerin, a skin conditioning agent.

Example 6

A microbicide and a flavor agent are combined with a carrier and applied to one or more surfaces of a condom. The condom may have between about 0.5 to about a 1.0 ml of a lubricious material on a surface(s) which includes between about 0.1 to about 5% (w/w) miconazole, a microbicide, and between about 0.1 to about 5.0% of a natural raspberry flavor.

Example 7

A microbicide and a fragrance are combined with a carrier and applied to one or more surfaces of a condom. The condom may have between about 0.5 to about 1.0 ml of a lubricious material on a surface(s) which includes between about 0.1 to about 5% (w/w) of miconazole, a microbicide, and between about 0.1 to about 10% (w/w) of an encapsulated floral fragrance.

Example 8

A sexual enhancement lubricant and a warming lubricant are combined with a carrier and applied to one or more surfaces of a condom. The condom may have between about 0.5 to about 1.0 ml of a lubricious material on a surface(s) which includes between about 0.1 to about 10% of menthol based sexual enhancement lubricant, and between about 0.1 to about 75% of a substantially anhydrous mixture of glycerin, propylene glycol and a surfactant, a mixture that generates warmth upon contact with moisture.

Example 9

A sexual enhancement lubricant and a vasodilator are combined with a carrier and applied to one or more surfaces of a condom. The condom may have between about 0.1 to about 1.0 ml of a lubricious material on a surface(s) which includes between about 0.1 to about 10% of a menthol based sexual enhancement lubricant and between about 0.1 and about 10% (w/w) of niacin, a vasodilator.

Example 10

A sexual enhancement lubricant and a spermicide are combined with a carrier and applied to one or more surfaces of a condom. The condom may have between about 0.1 to about 1.0 ml of a lubricious material on a surface(s) which includes between about 0.1 to about 10% of a menthol based sexual enhancement lubricant and between about 0.1 to about 10% (w/w) of nonoxynol-9, a spermicide.

Example 11

A sexual enhancement lubricant and a skin conditioner are combined with a carrier and applied to one or more surfaces of a condom. The condom may have between about 0.1 to about 1.0 ml of a lubricious material on a surface(s) which includes between about 0.1 to about 10% (w/w) of a menthol based sexual enhancement lubricant and between about 0.1 to about 10% (w/w) of glycerin, a skin conditioner.

Example 12

A sexual enhancement lubricant and a flavoring are combined with a carrier and applied to one or more surfaces of a condom. The condom may have between about 0.1 to about 1.0 ml of a lubricious material on a surface(s) which includes between about 0.1 to about 10% (w/w) of gingko biloba based sexual enhancement lubricant, and between about 0.1 and about 10% (w/w) of natural green tea flavoring.

Example 13

A sexual enhancement lubricant and a fragrance are combined with a carrier and applied to one or more surfaces of a condom. A condom may have between about 0.1 to about 1.0 ml of a lubricious material on a surface(s) which includes between about 0.1 to about 10% (w/w) of a menthol based sexual enhancement lubricant and between about 0.1 and about 10% (w/w) of natural mint fragrance.

Example 14

A warming lubricant and a vasodilator are combined with a carrier and applied to one or more surfaces of a condom. The condom may have between about 0.5 to about 1.0 ml of a lubricious material on a surface(s) which includes between about 0.1 to about 75% (w/w) of a substantially anhydrous mixture of glycerin, propylene glycol and a surfactant, a mixture that generates warmth upon contact with moisture, and between about 0.1 and about 10% (w/w) of niacin, a vasodilator.

Example 15

A warming lubricant and a spermicide are combined with a carrier and applied to one or more surfaces of a condom. The condom may have between about 0.5 to about 1.0 ml of a lubricious material on a surface which includes between about 0.1 to about 75% (w/w) of a substantially anhydrous mixture of glycerin, propylene glycol and a surfactant, a mixture that generates warmth upon contact with moisture, and between about 0.1 to about 10% (w/w) of nonoxynol-9, a spermicide.

Example 16

A warming agent and a skin conditioner are combined with a carrier and applied to one or more surfaces of a condom. The condom may have between about 0.1 to about 1.0 ml of a lubricious material on a surface(s) between about 0.1 to about 75% (w/w) of a substantially anhydrous mixture of glycerin, propylene glycol and a surfactant, a mixture that generates warmth upon contact with moisture, and between about 0.1 and about 10% (w/w) of aloe vera, a skin conditioner.

Example 17

A warming lubricant and a flavor are combined with a carrier and applied to one or more surfaces of a condom. The condom may have between about 0.1 to about 1.0 ml of a lubricious material on a surface(s) which includes between about 0.1 to about 75% (w/w) of a substantially anhydrous mixture of glycerin, propylene glycol and a surfactant, a mixture that generates warmth upon contact with moisture, and between about 0.1 and about 10% (w/w) of natural raspberry flavor.

Example 18

A warming lubricant and a fragrance are combined with a carrier and applied to one or more surfaces of a condom. The condom may have between about 0.1 to about 1.0 ml of a lubricious material on a surface(s) which includes between about 0.1 to about 75% (w/w) of a substantially anhydrous mixture of glycerin, propylene glycol and a surfactant, a mixture that generates warmth upon contact with moisture, and between about 0.1 and about 10% (w/w) of an encapsulated floral fragrance.

Example 19

A vasodilator and a spermicide are combined with a carrier and applied to one or more surfaces of a condom. The condom may have between about 0.1 to about 1.0 ml of a lubricious material on a surface(s) which includes between about 0.1 to about 10% (w/w) of niacin, a vasodilator, and between about 0.1 and about 10% (w/w) of nonoxynol-9, a spermicide.

Example 20

A vasodilator and a skin conditioner are combined with a carrier and applied to one or more of the surfaces of a condom. The condom may have between about 0.1 to about 1.0 ml of a lubricious material on a surface(s) which includes between about 0.1 to about 10% (w/w) of niacin, a vasodilator, and between about 0.1 and about 10% (w/w) of glycerin, a skin conditioner.

Example 21

A vasodilator and a flavorant are combined with a carrier and applied to one or more of the surfaces of a condom. The condom may have between about 0.1 to about 1.0 ml of a lubricious material on a surface(s) which includes between about 0.1 to about 10% (w/w) of niacin, a vasodilator, and between about 0.1 and about 10% (w/w) of a natural strawberry flavor.

Example 22

A vasodilator, and an encapsulated fragrance are combined with a carrier and applied to one or more surfaces of a condom. The condom may have between about 0.1 to about 1.0 ml of a lubricious material on a surface(s) which includes between about 0.1 to about 10% (w/w) of niacin, a vasodilator, and between about 0.1 and about 10% (w/w) of an encapsulated sandalwood fragrance.

Example 23

A spermicide and a skin conditioner are combined with a carrier and applied to one or more surfaces of a condom. The condom may have between about 0.1 to about 1.0 ml of a lubricious material on a surface(s) which includes between about 0.1 to about 10% (w/w) of nonoxynol-9, a spermicide, and between about 0.1 to about 10% (w/w) of aloe vera, a skin conditioner.

Example 24

A spermicide and a flavorant are combined with a carrier and applied to one or more of the surfaces of a condom. The condom may have between about 0.1 to about 1.0 ml aliquot of a lubricious material on a surface(s) which includes between about 0.1 to about 10% (w/w) of nonoxynol-9, a spermicide, and between about 0.1 and about 10% (w/w) of a natural raspberry flavor.

Example 25

A spermicide and a fragrance are combined with a carrier and applied to one or more surfaces of a condom. The condom may have between about 0.1 to about 1.0 ml of a lubricious material on a surface(s) which includes between about 0.1 to about 10% (w/w) of nonoxynol-9, a spermicide, and between about 0.1 and about 10% (w/w) of a frangibly encapsulated sandalwood fragrance.

Example 26

A skin conditioner and a flavorant are combined with a carrier and applied to one or more surfaces of a condom. The condom may have between about 0.1 to about 1.0 ml of a lubricious material on a surface(s) which includes between about 0.1 to about 10% (w/w) of aloe vera, a skin conditioner, and between about 0.1 and about 10% (w/w) of an encapsulated natural raspberry flavorant.

Example 27

A skin conditioner and a fragrance are combined with a carrier and applied to one or more of the surfaces of a condom. The condom may have between about 0.1 to about 1.0 ml aliquot of a lubricious material on a surface(s) which includes between about 0.1 to about 10% (w/w) of aloe vera, a skin conditioner, and between about 0.1 to about 10% (w/w) of a fresh wildflower fragrance.

Example 28

A flavoring and a fragrance are combined with a carrier and applied to one or more of the surfaces of a condom. The condom may have between about 0.1 to about 1.0 ml of a lubricious material on a surface(s) which includes between about 0.1 to about 10% (w/w) of a natural raspberry flavorant and between about 0.1 to about 10% (w/w) of a frangibly encapsulated sandalwood fragrance.

Example 29

A substantially anhydrous warming lubricant was prepared by mixing substantially equal amounts of propylene glycol and glycerin and a polysorbate surfactant. An L-arginine component (approximately 0.75% by weight of the overall mixture) and about 1.2% by weight water (of the overall mixture) were added to the warming lubricant. The L-arginine component was L-arginine base, which was substantially insoluble in the warming lubricant. A menthol component, menthyl lactate, was added in an amount of about 3.9% by weight. Preservative and pH adjuster components were also added. The mixture was applied to both sides of a condom and the resulting product is shown in FIGS. 1-4. The condom having L-arginine base in the warming lubricant produced an enhanced vasodilatory effect as compared to a condom having a water-based, non-warming lubricant, that contained dissolved L-arginine (in a greater amount, approximately 2% by weight, than that present in the warming lubricant of Example 29).

In accordance with the present invention, additional embodiments include the combinations set forth in Examples 1-28 and 29 wherein one or both of the ingredients are encapsulated. Still other embodiments include additional ingredients selected from a group including a microbicide, a sexual enhancement lubricant, a warming lubricant, a vasodilator, a spermicide, a skin conditioner, a flavoring and a fragrance. One or more of these additional ingredients may also be encapsulated for particular applications.

In some embodiments, the ingredients may form discrete and defined layers on the elastomeric layer, while in other embodiments the ingredients may form intermixed layers upon application to the elastomeric layer. Further, the encapsulated ingredients and the ingredients without encapsulation may also form discrete and defined layers or form intermixed layers upon application.

In some embodiments, the elastomeric layer is comprised of natural rubber latex, synthetic polyisoprene, guayule, polyurethane, combinations thereof and copolymers thereof, in the general shape of a male or female condom. Further embodiments are in the shape of abbreviated male condoms. Other embodiments utilize other substances (known in the art) to form the elastomeric layer. In some embodiments, the elastomeric layer is flexible and impermeable. In other embodiments, the elastomeric layer is contoured to have a larger diameter at the open end of the condom and/or the closed end of the condom. For example, some embodiments have a contoured portion wherein the diameter of the formed elastomeric layer is at least about 56 mm.

In accordance with one aspect of the invention, the elastomeric layer can be a thin film. For example, some embodiments utilize elastomeric layers having a thickness of less than about 0.05 mm. Other embodiments utilize elastomeric layers having a thickness of less than about 0.045 mm.

Yet other embodiments of the present invention have an elastomeric layer with a textured surface. Some embodiments include structural embellishments on the inner and/or outer surface of the elastomeric layer.

Further embodiments of the present invention include a packaging containing the condom, as otherwise described herein. Examples of packaging include, without limitation, wrappers, boxes, tubs having a sealed enclosure, and combinations thereof. In many embodiments, these packages may be formed from materials substantially resistant to the passage of air and/or moisture, as well as ingredients that may be present on the condom, so that ingredients present on the condom are retained, substantially unchanged, during storage prior to use.

One or more embodiments of the present invention include a method for preparing a condom having at least two ingredients having the following steps: forming an elastomeric layer in the shape of a male or female condom; and disposing at least two ingredients on the elastomeric layer. In one embodiment, the elastomeric layer is made of natural rubber latex, synthetic polyisoprene, guayule, polyurethane, combinations thereof and copolymers thereof. In other embodiments, the examples of the ingredients disposed on the elastomeric layer include a microbicide, a sexual enhancement lubricant, a warming lubricant, a vasodilator, a spermicide, a skin conditioner, a flavoring and a fragrance.

According to one embodiment of the present invention, the step of disposing at least two ingredients on the formed elastomeric layer includes disposition on both the inner and outer layer of the elastomeric layer. In other embodiments, the step of disposing at least two ingredients is limited to the inner or outer surface of the elastomeric layer. In accordance with one embodiment, the step of disposing at least two ingredients includes disposing one or more encapsulated ingredients. A further embodiment also includes disposing a film on one or both surfaces of the elastomeric layer prior to disposing the encapsulated ingredients. In some embodiments the film is a polymer such as polyurethane or any other material known in the art for adhering capsules to latex. In some embodiments, the ingredients disposed on the inner surface are different than the ingredients disposed on the outer surface. In other embodiments, the ingredients disposed on both the inner and outer surfaces are the same.

In other embodiments, the process for manufacturing condoms produces formed elastomeric layer having a defined thickness. In these embodiments, the elastomeric layer can be less than about 0.6 mm thick, while other embodiments have elastomeric layers having a thickness of less than about 0.045 mm.

Still other embodiments of the present invention include a formed elastomeric layer having a contoured shape. For example, in one embodiment, the open end of the condom has a larger diameter than the remaining length of the formed condom. In other embodiments, the closed end of the condom has a larger diameter than the remaining length of the condom. Yet other embodiments have enlarged diameters at both the closed and opened ends of the condom. In one or more embodiments, the enlarged or contoured portion of the condom has a diameter of about 56 mm. In yet other embodiments, the process produces condoms having an elastomeric layer with a textured surface or comprising other structural embellishments.

At least one embodiment of the present invention includes the step of packaging the finished condom. Specifically, in some embodiments, the formed elastomeric layer having at least two ingredients disposed thereon is packaged in a wrapper, box, tub with sealed enclosure, or any combination thereof. In some embodiments, the materials used in forming the package are selected from materials that can form packages that are substantially impermeable to the passage of air and moisture. The packaging materials include, but are not limited to, cellulosic materials, such as paper or paperboard; polymeric films and sheeting; metallic foils; and composite materials formed from these materials.

Processes that can be useful in making condoms in accordance with various aspects of the present invention are well known to those of ordinary skill in the art. Combinations discussed herein can also be applied to elastomeric gloves. One skilled in the art of making elastomeric film gloves will recognize that aspects of the methods, ingredients and coating materials useful in manufacture of gloves may be utilized for preparation of condoms. U.S. Patents and Published Applications disclosing processes that may be useful in various aspects of the present invention include: U.S. Pat. No. 7,235, 505 (Gromelski); U.S. Pat. No. 7,157,393 (Gromelski); U.S. Pat. No. 7,048,884 (Woodford); U.S. Pat. No. 7,037,579 (Hassan); U.S. Pat. No. 6,709,725 (Lai); U.S. Pat. No. 6,378,137 (Hassan); U.S. Pat. No. 6,352,666 (Nile); U.S. Pat. No. 6,347,409 (Nile); U.S. Pat. No. 6,306,514 (Weikel); U.S. Pat. No. 6,075,081 (Nile); U.S. Pat. No. 5,977,223 (Ryan); U.S. Pat. No. 5,888,441 (Milner); U.S. Pat. No. 5,323,544 (Osgood); U.S. Pat. No. 5,097,697 (Carnal); U.S. Pat. App. Pub. Nos. 2006/0070167 (Eng); 2006/0141165 (Hassan); 2005/0066414 (Yu); and 2004/0115250 (Loo), all of which are herein incorporated in their entireties by reference.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification, are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A condom, comprising:
   an elastomeric layer having an outer surface and an inner surface; and
   a coating disposed on the elastomeric layer, the coating comprising a substantially anhydrous liquid warming lubricant and a vasodilator disposed in the lubricant,
   wherein the at least one vasodilator is provided as locally concentrated particles that are suspended in and not dissolved in the liquid warming lubricant and are soluble in water, resulting in a highly effective and concentrated form on a user's skin upon contact with skin-generated moisture.

2. The condom of claim 1, wherein at least one of the locally concentrated particles is encapsulated.

3. The condom of claim 2, wherein the at least one locally concentrated particle is encapsulated in a water soluble capsule shell of gelatin, hydroxyalkyl cellulose, or combination thereof.

4. The condom of claim 1, wherein the warming lubricant comprises a glycerin, a polyhydric alcohol and non-ionic detergent in amounts effective to warm upon contact with skin-generated moisture.

5. The condom of claim 4, wherein the warming lubricant comprises substantially equal amounts of glycerin and a polyhydric alcohol.

6. The condom of claim 1, wherein a localized concentration of the at least one vasodilator is greater than the concentration of the vasodilator in the overall coating.

7. The condom of claim 1, wherein the warming lubricant comprises glycerin, propylene glycol, and a surfactant and the at least one vasodilator comprises at least one of niacin, ginger, L-arginine, or a nitric oxide precursor.

8. The condom of claim 1, wherein at least one of the locally concentrated particles is in solid phase.

9. The condom of claim 1, wherein the coating is disposed on the inner surface, the outer surface, or both.

10. The condom of claim 1, wherein the elastomeric layer is comprises of material selected from a group comprising natural rubber latex, synthetic polyisoprene, guayule, polyurethane, combinations thereof and copolymers thereof.

11. The condom of claim 1, wherein the coating further comprises a menthol component or a citric acid.

12. The condom of claim 1, wherein the condom is provided in a suitable package.

13. A condom, comprising:
    an elastomeric layer having an outer surface and an inner surface; and
    a coating disposed on one or both surfaces of the elastomeric layer, the coating comprising a substantially anhydrous liquid warming lubricant and an unencapsulated L-arginine component that is suspended in and not dissolved in the liquid warming lubricant and soluble in water and in a locally concentrated form,
    wherein the liquid warming lubricant and the L-arginine component together produce an enhanced effect upon contact with body moisture as compared to the use of the L-arginine component without the presence of the liquid warming lubricant.

14. The condom of claim 13, wherein the coating further comprises a menthol component or a citric acid.

15. The condom of claim 13, wherein the warming lubricant comprises substantially equal amounts of glycerin and a polyhydric alcohol.

16. The condom of claim 13, wherein the L-arginine component is provided in a solid phase.

17. A method of manufacturing a condom comprising:
    forming an elastomeric layer having an outer surface and an inner surface in the shape of a condom, wherein the elastomeric layer comprises a material selected from a group consisting of natural rubber latex, synthetic polyisoprene, guayule, polyurethane, combinations thereof or copolymers thereof; and
    disposing a coating on the inner surface, the outer surface, or both of the elastomeric layer, the coating comprising a substantially anhydrous liquid warming lubricant and at least one vasodilator, disposed in the lubricant, the at least one vasodilator being provided in a locally concentrated form that is suspended in and not dissolved in the liquid warming lubricant and soluble in water;
    wherein the warming lubricant and the at least one vasodilator together produce an enhanced effect upon contact of both with skin-generated moisture as compared with the use of the at least one vasodilator without the presence of the liquid warming lubricant.

18. The method of claim 17, comprising providing the at least one vasodilator as L-arginine in an unencapsulated solid phase.

19. The method of claim 17, comprising providing the at least one vasodilator in encapsulated form.

20. The method of claim 17, wherein the warming lubricant comprises a glycerin and a polyhydric alcohol.

21. A condom coating comprising:
    substantially anhydrous liquid warming lubricant applicable to one or more surfaces of an elastomeric condom; and
    locally concentrated, water-soluble particles comprising at least one vasodilator suspended in and not dissolved in the substantially anhydrous liquid warming lubricant.

22. The coating of claim 21, wherein the warming lubricant comprises glycerin, propylene glycol, and a surfactant.

23. The coating of claim 22, wherein the at least one vasodilator comprises at least one of niacin, ginger, L-arginine, or a nitric oxide precursor.

24. The coating of claim 21, wherein at least one of the particles is encapsulated.

25. The coating of claim 24, wherein the at least one encapsulated particle is/are encapsulated in a water soluble capsule shell of gelatin, hydroxyalkyl cellulose, or combination thereof.

26. The coating of claim 21, wherein the warming lubricant comprises a glycerin, a polyhydric alcohol and non-ionic detergent in amounts effective to warm upon contact with skin-generated moisture.

27. The coating of claim 26, wherein the warming lubricant comprises substantially equal amounts of glycerin and a polyhydric alcohol.

28. The coating of claim 21, wherein a localized concentration of the at least one vasodilator is greater than the concentration of the at least one vasodilator in the overall coating.

29. The coating of claim 21, wherein at least one of the particles is in solid phase.

30. The coating of claim 21, further comprising a menthol component or a citric acid.

31. A condom coating comprising:
   substantially anhydrous liquid warming lubricant applicable to one or more surfaces of an elastomeric condom; and
   an unencapsulated locally concentrated and water-soluble L-arginine component suspended in and not dissolved in the substantially anhydrous liquid warming lubricant,
   wherein the liquid warming lubricant and the L-arginine component together produce an enhanced effect upon contact with body moisture as compared to the use of the L-arginine component without the presence of the liquid warming lubricant.

32. The coating of claim 31, further comprising a menthol component or a citric acid.

33. The coating of claim 31, wherein the warming lubricant comprises substantially equal amounts of glycerin and a polyhydric alcohol.

34. The coating of claim 31, wherein the L-arginine component is in a solid phase.

35. A method of preparing a condom, the method comprising:
   providing a condom having an elastomeric layer with an outer surface and an inner surface;
   preparing a coating comprising suspending substantially without dissolving, in substantially anhydrous liquid warming lubricant, locally concentrated, water-soluble particles comprising at least one vasodilator; and
   disposing the coating on at least one of the outer surface and the inner surface of the condom,
   wherein the warming lubricant and the at least one vasodilator together produce an enhanced effect upon contact of both with skin-generated moisture as compared with the use of the at least one vasodilator without the presence of the liquid warming lubricant.

36. The method of claim 35, wherein the elastomeric layer comprises a material selected from a group consisting of natural rubber latex, synthetic polyisoprene, guayule, polyurethane, combinations thereof, and copolymers thereof.

37. The method of claim 35 comprising providing the at least one vasodilator as L-arginine in an unencapsulated solid phase.

38. The method of claim 35 comprising providing the at least one vasodilator in encapsulated form.

39. The method of claim 35, wherein the warming lubricant comprises a glycerin and a polyhydric alcohol.

* * * * *